United States Patent
Cavalla

(10) Patent No.: US 9,487,492 B2
(45) Date of Patent: Nov. 8, 2016

(54) DIBENZOTHIAZEPINE DERIVATIVES AND THEIR USE IN THE TREATMENT OF CNS DISORDERS

(75) Inventor: David Cavalla, Cambridge (GB)

(73) Assignee: NUMEDICUS LIMITED, Cambridgeshire (GB)

( * ) Notice: Subject to any disclaimer, the term of this patent is extended or adjusted under 35 U.S.C. 154(b) by 157 days.

(21) Appl. No.: 14/112,499

(22) PCT Filed: Apr. 16, 2012

(86) PCT No.: PCT/GB2012/050831
§ 371 (c)(1),
(2), (4) Date: Feb. 25, 2014

(87) PCT Pub. No.: WO2012/143703
PCT Pub. Date: Oct. 26, 2012

(65) Prior Publication Data
US 2014/0243317 A1    Aug. 28, 2014

(30) Foreign Application Priority Data

Apr. 18, 2011 (GB) .................................. 1106520.8
Aug. 1, 2011 (GB) .................................. 1113163.8

(51) Int. Cl.
| | | |
|---|---|---|
| A61K 31/554 | (2006.01) | |
| C07D 281/02 | (2006.01) | |
| C07D 417/12 | (2006.01) | |
| C07D 281/14 | (2006.01) | |

(52) U.S. Cl.
CPC ........... C07D 281/02 (2013.01); C07D 281/14 (2013.01)

(58) Field of Classification Search
CPC . A61K 31/554; C07D 281/02; C07D 417/12
USPC ..................... 514/211.13; 540/549
See application file for complete search history.

(56) References Cited

U.S. PATENT DOCUMENTS 3,872,102 A * 3/1975 Malen et al. ................. 540/549
2009/0209474 A1* 8/2009 Roegel et al. ................. 514/23
2009/0275541 A1  11/2009 Sullivan

FOREIGN PATENT DOCUMENTS

WO   WO-2005099714 A1   10/2005
WO   WO-2010070667 A2    6/2010

OTHER PUBLICATIONS

Salvadori C; "The pharmacokinetics of the antidepressant tianeptine and its main metabolite in healthy humans—influence of alcohol co-administration", Fundam. Clin. Pharmacol., vol. 4, (1990), pp. 115-125.

* cited by examiner

*Primary Examiner* — Brenda Coleman
(74) *Attorney, Agent, or Firm* — Frommer Lawrence & Haug LLP; William S. Frommer

(57) ABSTRACT

A compound of formula I:

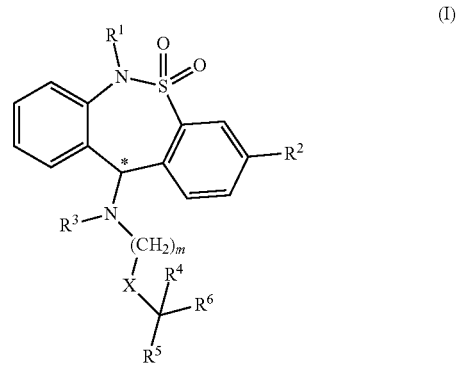

or a pharmaceutically or veterinarily acceptable salt thereof, or a pharmaceutically or veterinarily acceptable solvate of either entity, wherein: $R^1$, $R^2$, $R^3$, $R^4$, $R^5$, $R^6$, X and m are as defined herein.

30 Claims, 1 Drawing Sheet

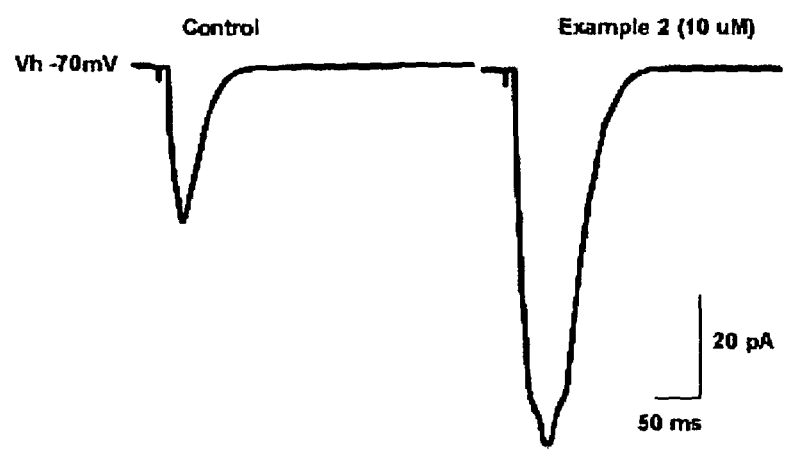

DIBENZOTHIAZEPINE DERIVATIVES AND THEIR USE IN THE TREATMENT OF CNS DISORDERS

CROSS-REFERENCE TO RELATED APPLICATIONS

This application is the National Stage application under 35 U.S.C. §371 of International Application No. PCT/GB2012/050831, filed Apr. 16, 2012, which claims the benefit of priority under 35 U.S.C. §119 of GB Patent Application No. 1106520.8, filed Apr. 18, 2011 and GB Patent Application No. 1113163.8, filed Aug. 1, 2011.

The present invention relates to pharmaceutically acceptable compounds, pharmaceutical compositions and the use of such compounds and compositions as a medicament, particularly a human medicament. In particular, although not exclusively, the compounds and compositions of the invention may be used in the treatment of a disorder or condition of the central nervous system (CNS). Additionally, the compounds of the invention typically exhibit enhanced metabolic stability and they may exert its therapeutic effect over a prolonged period of time with less side effects.

Tianeptine, as depicted below, is originally described in French patent 2,104,728 and has been reported that it may be used in the treatment of neurodegenerative pathologies, neuropathic pain, fibromyalgia, chronic fatigue syndrome and irritable bowel syndrome.

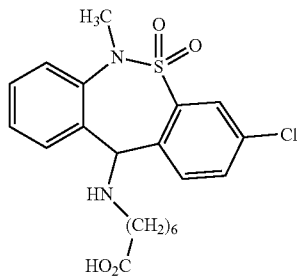

A major technical problem with the use of tianeptine as a medicament is that it is rapidly metabolized in the body and has a terminal half life of approximately 2.5 hours in humans (European Journal of Drug Metabolism and Pharmacokinetics 1990, 15(1): 69-74). In clinical practice it is administered three times a day. It is believed the rapid rate of metabolism of tianeptine in combination with the multiple daily dosage regime produces a high ratio of peak to trough concentrations of active agent in the body for a given frequency of administration and a given level of therapeutic cover, thereby producing undesirable side effects, such as: dry mouth; insomnia and vivid dreams; constipation; dizziness/syncope; drowsiness; and postural hypotension. It has recently been reported that tianeptine works by enhancing α-amino-3-(5-methyl-3-oxo-1,2-oxazol-4-yl)propanoic acid (AMPA) receptor mediated responses (Neurochem Int. 2011; 59(8): 1109-22).

The present invention is based on the discovery that compounds of the invention are typically potent enhancers of AMPA currents in the CNS and typically exhibit a significant increase in metabolic stability compared with tianeptine. Compounds that enhance AMPA currents have been claimed to facilitate learning and memory, improve attention span as well as reduce respiratory depression (Future Med. Chem. 2010; 2(5):877-91; Respir Physiol Neurobiol. 2009; 168(1-2):153-7). Suitably, the compounds of the invention may exert their therapeutic effect over a prolonged period of time, thereby enabling the patient to benefit from relief of symptoms for a longer period. Optimally, the patient may only require a once-a-day treatment regime, and as this will usually avoid missed treatments, better compliance is expected. In addition, treatments with a longer duration of action enable a lower ratio of peak to trough concentrations of active agent in the body for a given frequency of administration and a given level of therapeutic cover, which may result in reduced side effects associated with activity. Suitably, the compounds of the invention may exhibit reduced side effects compared to tianeptine, such side effects associated with tianeptine being: gastrointestinal disturbances, such as nausea, constipation and abdominal pain; headache; dizziness; drowsiness; and, insomnia and changes in dreaming.

BRIEF DESCRIPTION OF THE DRAWING

FIG. 1 depicts a representative electrophysiological recording of the compound of Example 2, which demonstrates the compound facilitates excitatory transmission in CA1 region of hippocampus.

DETAILED DESCRIPTION OF THE INVENTION

In accordance with a first aspect of the invention there is provided compounds of formula I,

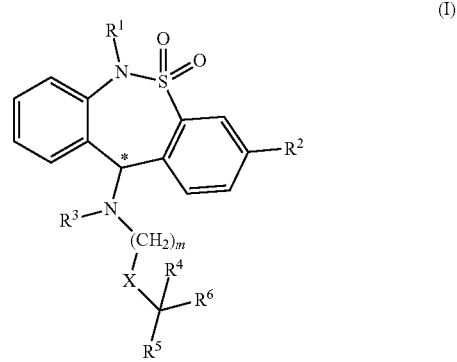

or a pharmaceutically or veterinarily acceptable salt thereof, or a pharmaceutically or veterinarily acceptable solvate of either entity, wherein:

$R^1$ and $R^3$ each independently represent, at each occurrence when used herein, H or $C_1$ to $C_6$ alkyl;

$R^2$ represents halo;

$R^4$ and $R^5$ each independently represent, at each occurrence when used herein, H, $C_1$ to $C_6$ alkyl, $C_2$ to $C_6$ alkenyl or $R^4$ and $R^5$ together form a 3, 4 or 5-membered alicyclic ring, wherein each of said alkyl and alkenyl groups are each independently optionally interrupted by one or more of —O—, —S— or —N($R^7$)— and/or substituted and/or terminated by one or more substituents selected from halo, —CN, —$NO_2$, —C(O)N($R^7$)$R^8$, —C(O)$R^7$, —C(O)O$R^7$, —N($R^7$)$R^8$, —O$R^7$;

$R^6$ represents —C(O)O$R^9$, —S(O)$_2$O$R^9$ or —C(O)N($R^7$)$R_8$;

X represents O, N($R^7$), S, S(=O), S(O)$_2$ or C($R^{10}$)($R^{11}$);

$R^7$ and $R^8$ each independently represent, at each occurrence when used herein, H or $C_1$ to $C_6$ alkyl;

$R^9$ represents H, $C_1$ to $C_6$ alkyl or $C_2$ to $C_6$ alkenyl, wherein each of said alkyl and alkenyl groups are each independently optionally interrupted by one or more of —O—, —S— or —N($R^7$)— and/or substituted and/or terminated by one or more substituents selected from halo, —CN, —NO$_2$, —C(O)N($R^7$)$R^8$, —C(O)$R^7$, —C(O)O$R^7$, —N($R^7$)$R^8$, —O$R^7$;

$R^{10}$ and $R^{11}$ each independently represent, at each occurrence when used herein, H, $C_1$ to $C_6$ alkyl, $C_2$ to $C_6$ alkenyl or $R^{10}$ and $R^{11}$ together form a 3, 4 or 5-membered alicylic ring, wherein each of said alkyl and alkenyl groups are each independently optionally interrupted by one or more of —O—, —S— or —N($R^7$)— and/or substituted and/or terminated by one or more substituents selected from halo, —CN, —NO$_2$, —C(O)N($R^7$)$R^8$, —C(O)$R^7$, —C(O)O$R^7$, —N($R^7$)$R^8$, —O$R^7$; and, m is an integer from 1 to 10 inclusive;

with the proviso that when X represents C($R^{10}$)($R^{11}$) then at least one of $R^4$, $R^5$, $R^{10}$, $R^{11}$ is not H.

As defined herein, the term "$C_1$ to $C_6$ alkyl", which $R^1$, $R^3$, $R^4$, $R^5$, $R^7$, $R^8$, $R^9$, $R^{10}$ and $R^{11}$ may each independently represent, may unless otherwise specified, when there is a sufficient number of carbon atoms, be linear or branched, be cyclic, acrylic or part cyclic/acyclic. Preferably, the alkyl group is an acyclic alkyl group, more preferably a linear alkyl group. Representative examples of alkyl groups include, but are not limited to, methyl, ethyl, n-propyl, iso-propyl, n-butyl, sec-butyl, iso-butyl, tert-butyl, n-pentyl, iso-pentyl, neo-pentyl and hexyl.

As defined herein, the term "$C_2$ to $C_6$ alkenyl", which $R^4$, $R^5$, $R^9$, $R^{10}$ and $R^{11}$ may each independently represent, means a $C_2$ to $C_6$ aliphatic hydrocarbyl group which includes at least one carbon to carbon double bond and may when there is a sufficient number of carbon atoms, be linear or branched, be cyclic, acyclic or part cyclic/acyclic. Preferably, the alkenyl group is an acyclic alkenyl group, more preferably a linear alkenyl group. Representative examples of alkenyl groups include, but are not limited to, ethenyl, propenyl, butenyl and pentenyl.

As defined herein, the term "alicyclic ring", which $R^4$ and $R^5$ together and $R^{10}$ and $R^{11}$ together may each independently represent, means an aliphatic hydrocarbyl group having a carbocyclic ring structure which may be saturated or unsaturated, preferably saturated. The term alicyclic ring excludes benzenoid, heterocyclic and other aromatic rings. Representative examples of 3, 4 or 5-membered alicyclic rings include, but are not limited to, cyclopropyl, cyclobutyl and cyclopentyl.

The term "halo", when used herein, includes fluoro, chloro, bromo and iodo.

For the avoidance of doubt each $R^1$, $R^3$, $R^4$, $R^5$, $R^7$, $R^8$, $R^9$, $R^{10}$ and $R^{11}$ group referred to herein is independent of other $R^1$, $R^3$, $R^4$, $R^5$, $R^7$, $R^8$, $R^9$, $R^{10}$ and $R^{11}$ groups, respectively. For example, if $R^4$ and $R^5$ both represent methyl substituted with —O$R^7$, the two individual —O$R^7$ substituents are independent of one another, and not necessarily identical (though this possibility is not excluded).

The pharmaceutically or veterinarily acceptable salts of the compounds of the invention are, for example, non-toxic acid addition salts formed with inorganic acids such as hydrochloric, hydrobromic, hydroiodic, sulphuric and phosphoric acid, with carboxylic acids or with organo-sulphonic acids. Examples include HCl, HBr, HI, sulphate or bisulphate, nitrate, phosphate or hydrogen phosphate, acetate, benzoate, succinate, saccharate, fumarate, maleate, lactate, malate, citrate, tartrate, fumarate, oxalate, gluconate, camsylate, methanesulphonate, ethanesulphonate, benzenesulphonate, p-toluenesulphonate and pamoate salts. The compounds of the invention can also provide pharmaceutically or veterinarily acceptable non-toxic base addition salts formed with bases, such as alkali metal and alkaline earth metal salts formed with inorganic bases such as sodium hydroxide, potassium hydroxide, calcium hydroxide, aluminium hydroxide, alkali and alkaline earth metal carbonates, or organic bases such as triethylamine, benzylamine, diethanolamine, tert-butylamine, dicyclohexylamine and arginine. For a review on suitable pharmaceutical salts see Berge et. al., J. Pharm., Sci., 66, 1-19, 1977. A highly preferred salt is the sodium salt.

The pharmaceutically or veterinarily acceptable solvates of the invention include the hydrates thereof.

The compounds of the invention, in particular the compounds of formula (I), contain one or more asymmetric carbon atoms and therefore exist in two or more stereoisomeric forms. As used herein, the enantiomeric forms of racemates refer to compositions consisting substantially of a single stereoisomer, i.e. substantially free of the other stereoisomer, that is containing at least 90%, preferably at least 95%, and more preferably at least 98% by weight of such a single stereoisomer.

In a compound of formula (I) the aliphatic carbon marked with an asterisk (*) denotes an asymmetric carbon atom and the absolute configuration about that carbon may be (R) or (S) as designated according to the Cahn Ingold Prelog system. The present invention includes the individual (R) and (S) enantiomers of the compounds of formula (I), in respect of the aliphatic carbon marked with an asterisk (*), and mixtures thereof (e.g. racemates). In accordance with a preferred embodiment, the present invention includes the individual (R) and (S) enantiomers of the compounds of formula (I), in respect of the aliphatic carbon marked with an asterisk (*).

An individual enantiomer of a compound of the invention, particularly a compound of formula (I) in respect of the aliphatic carbon marked with an asterisk (*), may be prepared from the corresponding optically pure intermediate or by resolution, either by HPLC of the racemate using a suitable chiral support or, where appropriate, by fractional crystallisation of the diastereoisomeric salts formed by reaction of the racemate with a suitable optically active acid or base.

It will be appreciated that the compounds of the invention may include one or more further asymmetric carbon atoms, in addition to the aliphatic carbon marked with an asterisk (*) in a compound of formula (I), depending on the identity of each of the substituent groups $R^1$, $R^3$, $R^4$, $R^5$, $R^7$, $R^8$, $R^9$, $R^{10}$ and $R^{11}$. For the avoidance of doubt, all stereoisomers and diastereoisomers of the compounds of the invention are included within the scope of the invention.

Where a compound of formula (I) contains an alkenyl group, cis (E) and trans (Z) isomerism may also occur. The present invention includes the individual structural isomers of the compounds of formula (I) and, where appropriate, the individual tautomeric forms thereof, together with mixtures thereof.

Also included in the invention are radiolabelled and isotopically labeled derivatives of the compounds of formula (I) which are suitable for biological studies. Examples of such derivatives include, but are not limited to, $^2$H, $^3$H, $^{11}$C, $^{13}$C, $^{14}$C, $^{15}$N, $^{18}$F, $^{35}$S and $^{36}$Cl.

Certain compounds of the invention may exist in multiple crystalline or amorphous forms. All physical forms and polymorphs are included within the scope of the invention.

Preferably, $R^1$ in a compound of formula (I) represents $C_1$ to $C_6$ alkyl, more preferably, $R^1$ represents $C_1$ to $C_4$ alkyl, even more preferably linear $C_1$ to $C_4$ alkyl. Most preferably, $R^1$ represents a methyl group.

Preferably, $R^2$ in a compound of formula (I) is fluoro or chloro, especially chloro.

Preferably, $R^3$ in a compound of formula (I) represents H or $C_1$ to $C_4$ alkyl. More preferably, $R^3$ represents H or linear $C_1$ to $C_4$ alkyl. Most preferably, $R^3$ represents H.

Preferably, $R^4$ and $R^5$ in a compound of formula (I) each independently represent H, $C_1$ to $C_6$ alkyl, $C_2$ to $C_6$ alkenyl or $R^4$ and $R^5$ together form a 3, 4 or 5-membered alicylic ring, wherein which alkyl group is each independently optionally interrupted by one or more of —O—, —S— or —N($R^7$)— and/or substituted and/or terminated by one or more substituents selected from halo, —C(O)N($R^7$)$R^8$, —C(O)$R^7$, —C(O)O$R^7$, —N(R)$R^8$, —O$R^7$. More preferably, $R^4$ and $R^5$ in a compound of formula (I) each independently represent H, $C_1$ to $C_6$ alkyl, $C_2$ to $C_6$ alkenyl or $R^4$ and $R^5$ together form a 3, 4 or 5-membered alicylic ring. Even more preferably, $R^4$ and $R^5$ each independently represent H, $C_1$ to $C_6$ alkyl or $C_2$ to $C_6$ alkenyl, even more preferably H or $C_1$ to $C_6$ alkyl, even more preferably H or $C_1$ to $C_4$ alkyl, even more preferably H or linear $C_1$ to $C_4$ alkyl, even more preferably H, methyl or ethyl. Preferably, $R^4$ and $R^5$ in a compound of formula (I), as defined herein, are both identical, most preferably both $R^4$ and $R^5$ in a compound of formula (I) represent H.

Preferably, $R^6$ in a compound of formula (I) represents —C(O)O$R^9$ or —C(O)N($R^7$)$R^5$, most preferably —C(O)O$R^9$.

Preferably, X in a compound of formula (I) represents O, N($R^7$), S, S(O)$_2$ or C($R^{10}$)($R^{11}$), more preferably O, S, S(O)$_2$ or C($R^{10}$)($R^{11}$), even more preferably O, S or S(O)$_2$, even more preferably O or S, most preferably O.

According to a preferred embodiment, X in a compound of formula (I) represents C($R^{10}$)$R^{10}$).

In accordance with an alternative preferred embodiment, X in a compound of formula (I) represents O, N($R^7$), S, S(=O), S(O)$_2$, preferably O, N(R), S or S(O)$_2$, more preferably O, S or S(O)$_2$, even more preferably O or S, most preferably O.

Suitably, when X in a compound of formula (I) represents C($R^{10}$)($R^{11}$) then at least one of $R^4$, $R^5$, $R^{10}$ and $R^{11}$ does not represent hydrogen, preferably at least one of $R^4$, $R^5$, $R^{10}$ and $R^{11}$ each independently represents $C_1$ to $C_6$ alkyl, $C_2$ to $C_6$ alkenyl, or $R^4$ and $R^5$ together or $R^{10}$ and $R^{11}$ together form a 3, 4 or 5-membered alicylic ring, more preferably at least one of $R^4$, $R^5$, $R^{10}$ and $R^{11}$ each independently represents $C_1$ to $C_6$ alkyl or $C_2$ to $C_6$ alkenyl, even more preferably at least one of $R^4$, $R^5$, $R^{10}$ and $R^{11}$ each independently represents $C_1$ to $C_6$ alkyl, even more preferably at least one of $R^4$, $R^5$, $R^{10}$ and $R^{11}$ each independently represents $C_1$ to $C_4$ alkyl, most preferably at least one of $R^4$, $R^5$, $R^{10}$ and $R^{11}$ each independently represents methyl or ethyl.

It will be appreciated when X in a compound of formula (I) represents C($R^{10}$)($R^{11}$) and both $R^4$ and $R^5$ represent H, then at least one of $R^{10}$ and $R^{11}$, as defined herein, does not represent hydrogen, preferably at least one of $R^{10}$ and $R^{11}$ each independently represents, preferably both of $R^{10}$ and $R^{11}$ represent, $C_1$ to $C_6$ alkyl, $C_2$ to $C_6$ alkenyl or $R^{10}$ and $R^{11}$ together form a 3, 4 or 5-membered alicylic ring, more preferably at least one of $R^{10}$ and $R^{11}$ each independently represents, preferably both of $R^{10}$ and $R^{11}$ represent, $C_1$ to $C_6$ alkyl or $C_2$ to $C_6$ alkenyl, even more preferably at least one of $R^{10}$ and $R^{11}$ each independently represents, preferably both of $R^{10}$ and $R^{11}$ represent, $C_1$ to $C_6$ alkyl, even more preferably at least one of $R^{10}$ and $R^{11}$ each independently represents, preferably both of $R^{10}$ and $R^{11}$ represent, $C_1$ to $C_4$ alkyl, even more preferably at least one of $R^{10}$ and $R^{11}$ each independently represents, preferably both of $R^{10}$ and $R^{11}$ represent, methyl or ethyl.

Preferably, $R^7$ when present in a compound of formula (I) represents H or $C_1$ to $C_4$ alkyl, more preferably H or linear $C_1$ to $C_4$ alkyl, most preferably H.

Preferably, $R^8$ when present in a compound of formula (I) represents H or $C_1$ to $C_4$ alkyl, more preferably H or linear $C_1$ to $C_4$ alkyl, most preferably H.

Preferably, $R^9$ when present in a compound of formula (I) represents H, $C_1$ to $C_6$ alkyl, or $C_2$ to $C_6$ alkenyl, wherein which alkyl group is each independently optionally interrupted by one or more of —O—, —S— or —N($R^7$)— and/or substituted and/or terminated by one or more substituents selected from halo, —C(O)N($R^7$)$R^8$, —C(O)$R^7$, —C(O)O$R^7$, —N($R^7$)$R^8$, —O$R^7$. More preferably, $R^9$ represents H, $C_1$ to $C_6$ alkyl or $C_2$ to $C_6$ alkenyl, even more preferably H or $C_1$ to $C_6$ alkyl, even more preferably H or $C_1$ to $C_4$ alkyl. Most preferably, $R^9$ represents hydrogen.

Preferably, $R^{10}$ and $R^{11}$ when present in a compound of formula (I) each independently represent H, $C_1$ to $C_6$ alkyl, $C_2$ to $C_6$ alkenyl or $R^{10}$ and $R^{11}$ together form a 3, 4 or 5-membered alicylic ring, wherein which alkyl group is each independently optionally interrupted by one or more of —O—, —S— or —N($R^7$)— and/or substituted and/or terminated by one or more substituents selected from halo, —C(O)N($R^7$)$R^8$, —C(O)$R^7$, —C(O)O$R^7$, —N($R^7$)$R^8$, —O$R^7$. More preferably, $R^{10}$ and $R^{11}$ when present in a compound of formula (I) each independently represent H, $C_1$ to $C_6$ alkyl, $C_2$ to $C_6$ alkenyl or $R^{10}$ and $R^{11}$ together form a 3, 4 or 5-membered alicylic ring. Even more preferably, $R^{10}$ and $R^{11}$ each independently represent H, $C_1$ to $C_6$ alkyl or $C_2$ to $C_6$ alkenyl, even more preferably H or $C_1$ to $C_6$ alkyl, even more preferably H or $C_1$ to $C_4$ alkyl, even more preferably H or linear $C_1$ to $C_4$ alkyl, even more preferably $R^{10}$ and $R^{11}$ each independently represent H, methyl or ethyl. Preferably, at least one of $R^{10}$ and $R^{11}$, as defined herein, more preferably both of $R^{10}$ and $R^{11}$, do not represent hydrogen. Even more preferably, both of $R^{10}$ and $R^{11}$ in a compound of formula (I), as defined herein, are identical.

Preferably, m in a compound of formula (I) is an integer from 1 to 8 inclusive, more preferably 1 to 6 inclusive, even more preferably 1 to 4 inclusive, even more preferably 2 to 4 inclusive. Most preferably, m is 4.

A preferred group of compounds of formula (I) are those wherein:

$R^1$ represents H or $C_1$ to $C_6$ alkyl;
$R^2$ represents halo;
$R^3$ represents H or $C_1$ to $C_6$ alkyl;
$R^4$ and $R^5$ each independently represent H, $C_1$ to $C_6$ alkyl, $C_2$ to $C_6$ alkenyl or $R^4$ and $R^5$ together form a 3, 4 or 5-membered alicylic ring;
$R^6$ represents —C(O)O$R^9$, —S(O)$_2$O$R^9$ or —C(O)N($R^7$)$R^8$;
$R^7$, $R^8$, $R^9$ when present each independently represent H or $C_1$ to $C_6$ alkyl;
X represents O, N(R), S, S(=O), S(O)$_2$ or C($R^{10}$)($R^{11}$), preferably O, S, S(O)$_2$ or C($R^{10}$)$R^{11}$);
$R^{10}$ and $R^{11}$ when present each independently represent H, $C_1$ to $C_6$ alkyl, $C_2$ to $C_6$ alkenyl or $R^{10}$ and $R^{11}$ together form a 3, 4 or 5-membered alicylic ring;
m is an integer from 1 to 8 inclusive;
with the proviso that when X represents C($R^{10}$)($R^{11}$) then at least one of $R^4$, $R^5$, $R^{10}$ and $R^{11}$ each independently represents $C_1$ to $C_6$ alkyl or $C_2$ to $C_6$ alkenyl, or $R^4$ and $R^5$ together form a 3, 4 or 5-membered alicylic ring, or $R^{10}$ and $R^{11}$ together form a 3, 4 or 5-membered alicylic ring.

A more preferred group of compounds of formula (I) are those wherein:
$R^1$ represents H or $C_1$ to $C_6$ alkyl;
$R^2$ represents halo;
$R^3$ represents H or $C_1$ to $C_6$ alkyl;
$R^4$ and $R^5$ each independently represent H, $C_1$ to $C_6$ alkyl or $C_2$ to $C_6$ alkenyl, preferably H or $C_1$ to $C_6$ alkyl;
$R^6$ represents —C(O)OR$^9$, —S(O)$_2$OR$^9$ or —C(O)N(R$^7$)R$^8$;
$R^7$, $R^8$, $R^9$ when present each independently represent H or $C_1$ to $C_6$ alkyl;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ and $R^{11}$ when present each independently represent H, $C_1$ to $C_6$ alkyl or $C_2$ to $C_6$ alkenyl, preferably H or $C_1$ to $C_6$ alkyl;
m is an integer from 1 to 8, preferably 1 to 4, inclusive;
with the proviso that when X represents C(R$^{10}$)(R$^{11}$) then at least one of $R^4$, $R^5$, $R^{10}$ and $R^{11}$ each independently represents $C_1$ to $C_6$ alkyl or $C_2$ to $C_6$ alkenyl, preferably $C_1$ to $C_6$ alkyl, more preferably methyl or ethyl.

An even more preferred group of compounds of formula (I) are those wherein:
$R^1$ represents H or $C_1$ to $C_6$ alkyl;
$R^2$ represents halo;
$R^3$ represents H or $C_1$ to $C_6$ alkyl;
$R^4$ and $R^5$ each independently represent H, $C_1$ to $C_6$ alkyl or $C_2$ to $C_6$ alkenyl, preferably H or $C_1$ to $C_6$ alkyl;
$R^6$ represents —C(O)OR$^9$, —S(O)$_2$OR$^9$ or —C(O)N(R$^7$)R$^8$;
$R^7$, $R^8$, $R^9$ when present each independently represent H or $C_1$ to $C_6$ alkyl;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ when present represents H, $C_1$ to $C_6$ alkyl or $C_2$ to $C_6$ alkenyl, preferably H or $C_1$ to $C_6$ alkyl;
$R^{11}$ when present represents $C_1$ to $C_6$ alkyl or $C_2$ to $C_6$ alkenyl, preferably $C_1$ to $C_6$ alkyl; and,
m is an integer from 1 to 8, preferably 1 to 4, inclusive.

An even more preferred group of compounds of formula (I) are those wherein:
$R^1$ represents H or $C_1$ to $C_6$ alkyl;
$R^2$ represents halo;
$R^3$ represents H or $C_1$ to $C_6$ alkyl;
$R^4$ and $R^5$ each independently represent H or $C_1$ to $C_6$ alkyl, preferably both of $R^4$ and $R^5$ represent H;
$R^6$ represents —C(O)OR$^9$, —S(O)$_2$OR$^9$ or —C(O)N(R)R$^8$;
$R^7$, $R^8$, $R^9$ when present each independently represent H or $C_1$ to $C_6$ alkyl;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ and $R^{11}$ when present each independently represent $C_1$ to $C_6$ alkyl; and,
m is an integer from 1 to 8, preferably 1 to 4, inclusive.

An even more preferred group of compounds of formula (I) are those wherein:
$R^1$ represents H or $C_1$ to $C_6$ alkyl;
$R^2$ represents halo;
$R^3$ represents H or $C_1$ to $C_6$ alkyl;
$R^4$ and $R^5$ each independently represent H or $C_1$ to $C_6$ alkyl, preferably both of $R^4$ and $R^5$ represent H;
$R^6$ represents —C(O)OR$^9$, —S(O)$_2$OR$^9$ or —C(O)N(R$^7$)R$^8$;
$R^7$ and $R^8$ when present each independently represent H or $C_1$ to $C_6$ alkyl;
$R^9$ when present represents H;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ and $R^{11}$ when present each independently represent $C_1$ to $C_6$ alkyl; and,
m is an integer from 1 to 8, preferably 1 to 4, inclusive.

An even more preferred group of compounds of formula (I) are those wherein;
$R^1$ represents $C_1$ to $C_6$ alkyl, preferably methyl;
$R^2$ represents chloro;
$R^3$ represents H or $C_1$ to $C_6$ alkyl, preferably H;
$R^4$ and $R^5$ each independently represent H or $C_1$ to $C_6$ alkyl, preferably both of $R^4$ and $R^5$ represent H;
$R^6$ represents —C(O)OR$^9$ or —C(O)N(R$^7$)R$^8$;
$R^7$ and $R^8$ when present each independently represent H or $C_1$ to $C_6$ alkyl;
$R^9$ when present represents H;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ and $R^{11}$ when present each independently represent $C_1$ to $C_6$ alkyl; and,
m is an integer from 1 to 8, preferably 1 to 4, inclusive.

An even more preferred group of compounds of formula (I) are those wherein:
$R^1$ represents $C_1$ to $C_6$ alkyl, preferably methyl;
$R^2$ represents chloro;
$R^3$ represents H or $C_1$ to $C_6$ alkyl, preferably H;
$R^4$ and $R^5$ each independently represent H or $C_1$ to $C_6$ alkyl, preferably both of $R^4$ and $R^5$ represent H;
$R^6$ represents —C(O)OR$^9$;
$R^9$ represents H or $C_1$ to $C_6$ alkyl, preferably H;
X represents O, N(R$^7$), S, S(=O), S(O)$_2$ or C(R$^{10}$)(R$^{11}$), preferably O, S, S(O)$_2$ or C(R$^{10}$)(R$^{11}$), more preferably O, S or S(O)$_2$, even more preferably O;
$R^{10}$ and $R^{11}$ when present each independently represent $C_1$ to $C_6$ alkyl; and,
m is an integer from 1 to 8, preferably 1 to 4, inclusive.

An even more preferred group of compounds of formula (I) are those wherein:
$R^1$ represents $C_1$ to $C_6$ alkyl, preferably methyl;
$R^2$ represents chloro;
$R^3$ represents H or $C_1$ to $C_6$ alkyl, preferably H;
$R^4$ and $R^5$ each independently represent H or $C_1$ to $C_6$ alkyl, preferably both of $R^4$ and $R^5$ represent H;
$R^6$ represents —C(O)OR$^9$;
$R^9$ represents H;
X represents O, S, S(O)$_2$ or C(R$^{10}$)(R$^{11}$), preferably O, S or S(O)$_2$, more preferably O;
$R^{10}$ and $R^{11}$ when present each independently represent $C_1$ to $C_6$ alkyl; and,
m is an integer from 1 to 8, preferably 1 to 4, inclusive.

An even more preferred group of compounds of formula (I) are those wherein:
$R^1$ represents $C_1$ to $C_6$ alkyl, preferably methyl;
$R^2$ represents chloro;
$R^3$ represents H or $C_1$ to $C_6$ alkyl, preferably H;
$R^4$ and $R^5$ each independently represent H or $C_1$ to $C_6$ alkyl, preferably both of $R^4$ and $R^5$ represent H;
$R^6$ represents —C(O)OR$^9$;

R⁹ represents H;

X represents O, S or S(O)₂, preferably O; and, m is an integer from 1 to 8, preferably 1 to 4, inclusive.

A most preferred group of compounds of formula (I) are those wherein:

R¹ represents $C_1$ to $C_6$ alkyl, preferably methyl;

R² represents chloro;

R³ represents H or $C_1$ to $C_6$ alkyl, preferably H;

R⁴ and R⁵ each independently represent H or $C_1$ to $C_6$ alkyl, preferably both of R⁴ and R⁵ represent H;

R⁶ represents —C(O)OR⁹;

R⁹ represents H;

X represents O; and, m is an integer from 1 to 4, preferably 2 to 4, inclusive, more preferably m is 4.

An alternative preferred group of compounds of formula (I) are those wherein:

R¹ represents $C_1$ to $C_6$ alkyl, preferably methyl;

R² represents chloro;

R³ represents H or $C_1$ to $C_6$ alkyl, preferably H;

R⁴ and R⁵ each independently represent H, methyl or ethyl;

R⁶ represents —C(O)OR⁹ or —S(O)₂OR⁹;

R⁹ represents H;

X represents O, N(R¹⁰), S, S(=O), S(O)₂ or C(R¹⁰)(R¹¹);

R¹⁰ and R¹¹ when present each independently represent H or $C_1$ to $C_6$ alkyl, preferably H, methyl or ethyl;

m is an integer from 1 to 4, inclusive;

with the proviso that when X represents C(R¹⁰)(R¹¹) then at least one of R⁴, R⁵, R¹⁰ and R¹¹ each independently represents methyl or ethyl.

Preferred compounds of the invention include the compounds of the examples described hereinafter.

Thus, according to a further aspect of the invention, there is provided a compound of formula (I) which, irrespective of any of the foregoing definitions and/or provisos, is:

2-(2-((3-chloro-6-methyl-5,5-dioxido-6,11-dihydrodibenzo[c,f][1,2]thiazepin-11-yl)amino)ethoxy)acetic acid;

t-butyl 2-(4-((3-chloro-6-methyl-5,5-dioxido-6,11-dihydrodibenzo[c,f][1,2]thiazepin-11-yl)amino)butoxy)acetate;

2-(4-((3-chloro-6-methyl-5,5-dioxido-6,11-dihydrodibenzo[c,f][1,2]thiazepin-11-yl)amino)butoxy)acetic acid;

2-((2-((3-chloro-6-methyl-5,5-dioxido-6,11-dihydrodibenzo[c,f][1,2]thiazepin-11-yl)amino)ethyl)thio)acetic acid;

2-((2-((3-chloro-6-methyl-5,5-dioxido-6,11-dihydrodibenzo[c,f][1,2]thiazepin-11-yl)amino)ethyl)sulfonyl)acetic acid;

5-((3-chloro-6-methyl-5,5-dioxido-6,11-dihydrodibenzo[c,f][1,2]thiazepin-11-yl)amino)pentanamide; and, ethyl 5-((3-chloro-6-methyl-5,5-dioxido-6,11-dihydrodibenzo[c,f][1,2]thiazepin-11-yl)amino)-3,3-dimethylpentanoate.

The most preferred compound of the invention is 2-(4-((3-chloro-6-methyl-5,5-dioxido-6,11-dihydrodibenzo[c,f][1,2]thiazepin-1-yl)amino)butoxy)acetic acid, particularly the (R) and (S) enantiomeric forms thereof in respect of the aliphatic carbon atom labeled with an asterisk in formula (I).

In a further aspect, the present invention provides processes for the preparation of compounds of formula (I), their pharmaceutically and veterinarily acceptable salts, and pharmaceutically and veterinarily acceptable solvates of either entity, as illustrated below.

The following processes are illustrative of the general synthetic procedures which may be adopted in order to obtain the compounds of the invention.

A compound of formula (I) may be prepared from a compound of formula (II):

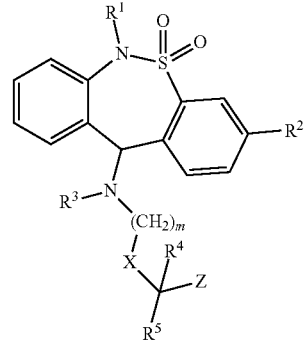

(II)

wherein R¹, R², R³, R⁴, R⁵, X and m are as previously defined for formula (I), and Z represents —C≡CH or —SH, by oxidation of the —C≡CH group or the thiol group in the compound of formula (II).

The oxidation of the —C≡CH group, when present, in the compound of formula (II) is generally conducted at room temperature, preferably in the presence of a suitable solvent such as aqueous acetonitrile, using an oxidising agent such as sodium metaperiodate and ruthenium trichloride.

The oxidation of the —C≡CH group in the compound of formula (II) produces a compound of formula (I) where R⁶ represents —C(O)OR⁹ and R⁹ represents hydrogen. Such compounds of formula (I) may be readily converted to other compounds of formula (I) by standard substituent and/or functional group interconversions and transformations. For example, a compound of formula (I) where R⁶ represents —C(O)OH may be converted to a compound of formula (I) where R⁶ represents —C(O)OR⁹ and R⁹ represents $C_1$ to $C_6$ alkyl or $C_2$ to $C_6$ alkenyl, as defined herein, by esterification using R⁹OH using reaction conditions in accordance with techniques which are well known to those skilled in the art (for instance in well known text books of synthetic organic chemistry such as 'Practical Synthetic Organic Chemistry: Reactions, Principles, and Techniques' by Stéphane Caron (Wiley-Blackwell 2011)). Similarly, a compound of formula (I) where R⁶ represents —C(O)OH may be converted to a compound of formula (I) where R⁶ represents —C(O)N(R⁷)R⁸, as defined herein, by forming an activated carbonyl compound, e.g. by reaction with thionyl chloride, followed by reaction with an amine of formula HN(R⁷)R⁸. Suitably, a compound of formula (I) where X represents SO₂ or S(=O) may be formed during oxidation of the —C≡CH group in a compound of formula (II) where X represents S.

The oxidation of the thiol group, when present, in the compound of formula (II) is generally conducted at ambient temperature or slightly above, preferably in the presence of a suitable solvent such as methanol, using an oxidising agent such as sodium hypochlorite, hydrogen peroxide, ozone or oxygen in basic conditions.

The oxidation of the thiol group in the compound of formula (II) produces a compound of formula (I) where R⁶ represents —S(O)₂OR⁹ and R⁹ represents hydrogen. Such compounds of formula (I) may be readily converted to other compounds of formula (I) by standard substituent and/or functional group interconversions and transformations. For example, a compound of formula (I) where R⁶ represents —S(O)₂OH may be converted to a compound of formula (I)

where $R^6$ represents —S(O)$_2$OR$^9$ and $R^9$ represents $C_1$ to $C_6$ alkyl or $C_2$ to $C_6$ alkenyl, as defined herein, by esterification using $R^9$OH using reaction conditions in accordance with techniques which are well known to those skilled in the art (for instance in well known text books of synthetic organic chemistry such as 'Practical Synthetic Organic Chemistry: Reactions, Principles, and Techniques' by Stéphane Caron (Wiley-Blackwell 2011)).

A compound of formula (II) may be prepared from a compound of formula (III):

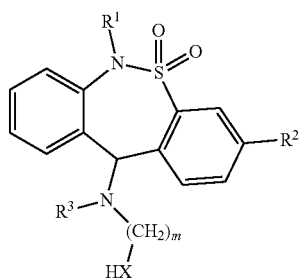

(III)

wherein $R^1$, $R^2$, $R^3$, and m are as previously defined for formula (II), X represents O, N(R$^7$) or S, and $R^7$ is as previously defined for formula (I), by reaction with a compound of formula (IV):

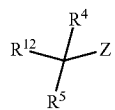

(IV)

wherein $R^4$, $R^5$, and Z are as previously defined for formula (II), and $R^{12}$ represents a suitable leaving group, e.g. halo (preferably chloro, bromo or iodo). The reaction, particularly when X represents O, is generally conducted at room temperature, preferably in the presence of a suitable solvent such as tetrahydrofuran (THF), using an excess of (IV) and a suitable base such as sodium hydride. It will be appreciated, that when Z represents —SH in a compound of formula (IV) then it may be desirable to protect the thiol group with a suitable protecting group.

A compound of formula (III) may be prepared from a compound of formula (V):

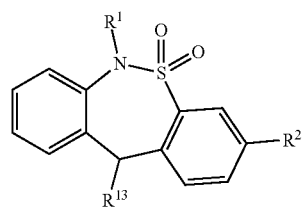

(V)

wherein $R^1$ and $R^2$ are as previously defined for formula (III) and $R^{13}$ represents a suitable leaving group, e.g. halo (preferably chloro, bromo or iodo), by reaction with a compound of formula (VI):

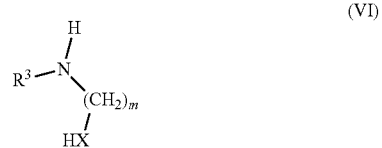

(VI)

wherein $R^3$, X and m are as previously defined for formula (III). The reaction, particularly when X represents O, is generally conducted at reflux in the presence of a suitable solvent, such as ethanol. It will be appreciated, that X in a compound of formula (VI) may be protected with a suitable protecting group, if desired or required.

An alternative, generally applicable, synthetic route to the compounds of formula (I) involves a reductive animation reaction.

Thus a compound of formula (I) may also be prepared by reducing a compound of formula (VII):

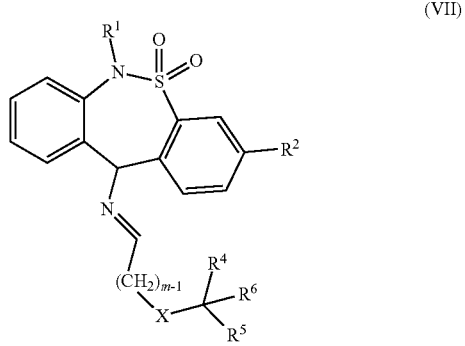

(VII)

wherein $R^1$, $R^2$, $R^4$, $R^5$, $R^6$, X and m are as previously defined for a compound of formula (I).

The reaction is generally conducted at room temperature in the presence of a suitable solvent, such as dichloromethane, and a hydride reducing agent such as sodium triacetoxyborohydride.

It will be appreciated by those skilled in the art that $R^6$ in a compound of formula (VII), and hence also in a compound of formulae (IX) and (X) as detailed hereinafter, may be a suitably protected derivative thereof. Suitably, when $R^6$ represents —C(O)OR$^9$, —S(O)$_2$OR$^9$ or —C(O)N(R$^7$)R$^8$ in a compound of formula (VII) and $R^9$ represents H, and at least one of $R^7$ and $R^8$, typically when both of $R^7$ and $R^8$, represent H, then a suitable protecting group strategy for the carboxylic acid, sulphonic acid or amide group may be employed. The protecting group is typically removed following reduction of the imine bond in a compound of formula (VII).

A compound of formula (VII) may be prepared from a compound of formula (VIII):

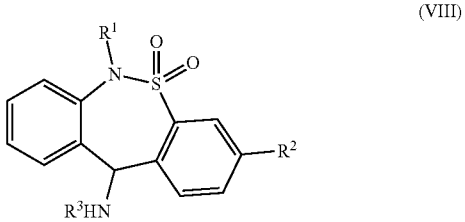

(VIII)

wherein $R^1$ and $R^2$ are as previously defined for formula (VII), and $R^3$ represents H, by reaction with a compound of formula (IX):

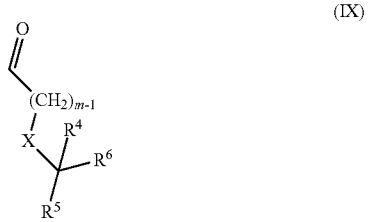

(IX)

wherein $R^4$, $R^5$, $R^6$, X and m are as previously defined for a compound of formula (VII). The reaction is generally conducted at room temperature in a suitable solvent, such as dichloromethane, using an excess of a compound of formula (IX) and a suitable base e.g. triethylamine.

A compound of formula (IX) may be prepared by oxidation of a compound of formula (X):

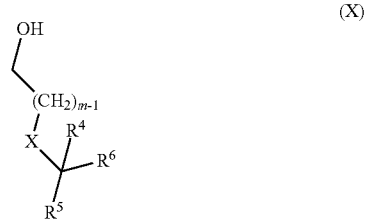

(X)

wherein $R^4$, $R^5$, $R^6$, X and m are as previously defined for formula (IX). The reaction is generally conducted in a suitable solvent such as dichloromethane, at 0° C. and using a suitable oxidizing agent such as Dess-Martin periodinane.

The intermediate compounds of formula (II), (III) and (VII) are also within the scope of the invention.

The compounds of formulae (V), (VI), (VIII) and (X), when neither commercially available nor subsequently described, can be obtained either by analogy with the processes described in the Preparations section or by conventional synthetic procedures in accordance with standard textbooks on organic chemistry or literature precedent, from readily accessible starting materials using appropriate reagents and reaction conditions.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in said synthetic steps. Moreover, persons skilled in the art will be aware of variations of, and alternatives to, those processes described hereinafter in the Examples and Preparations sections which allow the compounds defined by formula (I) to be obtained.

It will be appreciated that various standard substituent or functional group interconversions and transformations within certain compounds of formula (I) will provide other compounds of formula (I). Examples include removal of the alkyl group where $R^6$ represents —C(O)OR$^9$ and $R^9$ represents $C_1$ to $C_6$ alkyl to form the corresponding carboxylic acid (see conversion of Example 2(c) to Example 2(d) and Example 6(d) to Example 6(e)), oxidation of X, where X represents S, to form a compound of formula (I) where X represents S(O)$_2$ (see Example 4).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it may be desirable to protect include hydroxy, amino, thiol, carboxylic acid, sulphonic acid and amide. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g., methyl- and ethylcarbonyl). Suitable protecting groups for amino include tert-butyloxycarbonyl, 9-fluorenylmethoxycarbonyl or benzyloxycarbonyl. Suitable protecting groups for carboxylic acid and sulphonic acid include $C_{1-6}$ alkyl or benzyl esters. Suitable protecting groups for thiols include t-butyl or trityl groups, or the formation of thioesters, thiocarbonates and thiocarbamates. The protection and deprotection of functional groups may take place before or after any of the reaction steps described hereinbefore. Protecting groups may be removed in accordance with techniques which are well known to those skilled in the art. The use of protecting groups is fully described in "Protective Groups In Organic Chemistry" by JWF McOmie, Plenum Press (1973), and "Protective Groups in Organic Synthesis", 2nd edition, TW Greene & PGM Wutz, Wiley-Interscience (1991).

Illustrative of protecting group strategies are the routes to the syntheses of compounds of formulae (II), (IV), (VI), (VII), (IX) and (X).

The pharmaceutically acceptable acid addition salts of the compounds of formula (I) may also be prepared in a conventional manner. For example, a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of formula (I) may act as prodrugs of other compounds of formula (I).

All protected derivatives, and prodrugs, of compounds of formula (I) are included within the scope of the invention.

Medical Use

The compounds of the invention are useful because they possess pharmacological activity in animals, especially mammals, including humans. They are therefore indicated as pharmaceuticals, as well as for use as animal medicaments Thus according to a further aspect of the invention there is provided a compound of formula (I), or a pharmaceutically acceptable salt thereof, or a pharmaceutically acceptable solvate of either entity for use as a human medicament.

Thus according to a further aspect of the invention there is provided a compound of formula (I), or a pharmaceutically acceptable salt thereof, or a pharmaceutically acceptable solvate of either entity for use as an animal medicament.

In particular, the compounds of formula (I) have been found to be potent enhancers of AMPA currents in the Central Nervous System (CNS). The compounds of formula (I), particularly those which are penetrant in the brain, are therefore suitable for the treatment of a disease (i.e. disorder or condition) of the central nervous system such as depression, anxiety, bipolar disorder, schizophrenia, chronic fatigue syndrome, sleep apnea, cognitive dysfunction, Alzheimer's disease, Huntington's disease, Parkinson's disease, attention deficit hyperactivity disorder (ADHD), autism, Fragile X syndrome, fibromyalgia or neuropathic or inflammatory pain.

Thus the invention provides a method of treating or preventing a medical condition or disorder of the CNS in an animal (e.g. a mammal, including a human being) which comprises administering a therapeutically effective amount of a compound of the invention to a mammal in need of such treatment.

Suitably, the invention provides the use of a compound of the invention for the treatment of a medical condition or disorder of CNS in an animal (e.g. a mammal, including a human being).

Additionally, the compounds of formula (I), particularly when they are distributed throughout the body predominantly external to the central nervous system, are suitable for the treatment of disorders mediated by pathways mainly (or partly) outside the CNS. The compounds of formula I are therefore suitable for the treatment of: a disease (i.e. disorder or condition) of the gastrointestinal system, such as irritable bowel syndrome; a disease or condition of the airways, including asthma, hypoventilation (including respiratory depression for instance after surgery, or induced by drugs, such as opiates or anaesthetics), cough, chronic obstructive pulmonary disease (COPD), cystic fibrosis, pulmonary fibrosis, allergic rhinitis, pulmonary hypertension or lung carcinoma associated with concomitant COPD; and, a disease or condition of the skin such as atopic dermatitis.

Thus the invention provides a method of treating or preventing a medical condition or disorder of the gastrointestinal system, of the airways and/or of the skin in an animal (e.g. a mammal, including a human being) which comprises administering a therapeutically effective amount of a compound of the invention to a mammal in need of such treatment.

Suitably, the invention provides the use of a compound of the invention for the treatment of a medical condition or disorder of the gastrointestinal system, of the airways and/or of the skin in an animal (e.g. a mammal, including a human being).

By the term "treatment", we include both therapeutic (curative), palliative and prophylactic treatment.

By the term "disease", we include any condition or disorder that damages or interferes with the normal function of a cell, tissue or organ in an animal e.g. a mammal, including a human being.

Particularly preferred conditions or disorders which a compound of formula (I) may be used to treat or prevent are conditions of the CNS as detailed herein.

Pharmaceutical Preparations

The compounds of the invention will normally be administered orally or by any parenteral route in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of a condition or disorder for which the compounds of the invention are indicated. Examples of suitable additional drugs for coadministration with the compounds of the invention for respiratory diseases include: steroids such as beclomethasone, budesonide, betamethasone and fluticasone; mucolytics; matrix metalloproteinase inhibitors (MMPIs); leukotriene D4 antagonists; antibiotics; antineoplastics; antitussives; nicotine; PDE4 inhibitors; PDE3/4 inhibitors; elastase inhibitors; immunosuppressants such as cyclosporine A, tacrolimus, methotrexate and pimecrolimus; beta-2 adrenergic agonists such as salbutamol, salmeterol, formoterol and fenoterol; antimuscarinics such as tiotropium, ipratropium, aclidinium, clidinium and glycopyrrolate; and sodium cromoglycate. Examples of suitable additional drugs for coadministration with the compounds of the invention for CNS diseases include: anti-depressants such as fluoxetine, paroxetine or mirtazapine; cognition enhancers such as memantine, donepezil or miotine; antipsychotics such as clozapine, olanzepine or lithium; analgesics such as morphine, meperidine, fentanyl or oxycodone; or other CNS drugs such as modafinil.

The compounds of the invention, their pharmaceutically acceptable salts, and pharmaceutically acceptable solvates of either entity can be administered alone but, in human therapy will generally be administered in admixture with a suitable pharmaceutical excipient, diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via intracavernosal injection. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as poly-vinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to hydroxypropylmethyl cellulose, methyl cellulose, sodium carboxymethylcellulose, ethyl cellulose, cellulose acetate. polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form e.g. upon the surface or coating. Formulation technology may be used to provide a sustained release oral dosage form containing a compound of the invention having a duration of action of more than 12, preferably more than 18, most preferably more than 24 hours.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, polyethylene glycol, fumed silica, silicon dioxide, sodium starch glycolate, sorbitol, xylitol.

The compounds of the invention can also be administered parenterally, for example, intracavernosally, intravenously, intra-arterially, intraperitoneally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of formula (I) or salts or solvates thereof will usually be from 1 to 250 mg, preferably 5 to 100 mg, most preferably 10 to 50 mg (in single or divided doses).

Thus, for example, tablets or capsules of the compounds of the invention or salts or solvates thereof may contain from 2.5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Example Tablet Formulation

In general a tablet formulation could typically contain between about 2.5 mg and 250 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Compound of Example 2 | 10 |
| Lactose | 65 |
| Starch | 21 |
| Croscarmellose Sodium | 3 |
| Magnesium Stearate | 1 |

The compounds of the invention can also be administered intranasally or by inhalation and are conveniently delivered in the form of a dry powder inhaler or an aerosol spray presentation from a pressurised container pump, spray or nebuliser with the use of a suitable propellant, e.g. dichlorodifluoromethane, trichlorofluoromethane, a hydrofluoroalkane such as 1,1,1,2-tetrafluoroethane, carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the formula (I) for delivery to the patient. The overall daily dose with an aerosol will be in the range of from 1 to 50 mg which may be administered in a single dose or more usually in divided doses throughout the day.

The compounds of the invention may also be formulated for delivery via an atomiser. Formulations for atomiser devices may contain the following ingredients as solubilisers, emulsifiers or suspension agents: water; ethanol; glycerol; propylene glycol; low molecular weight polyethylene glycols; sodium chloride; fluorocarbons; sorbitan trioleate; and, oleic acid. Alternatively, the compounds of the invention or salts or solvates thereof can be administered in the form of a suppository or pessary, or they may be applied topically in the form of a gel, hydrogel lotion, solution, cream, ointment or dusting powder. The compounds of the invention or salts or solvates thereof may also be dermally administered. The compounds of the invention or salts or solvates thereof may also be transdermally administered, for example, by the use of a skin patch. They may also be administered by the ocular or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention or salts or solvates thereof can be formulated as a suitable ointment containing the active compound suspended or dissolved in, for example, a mixture with one or more of the following: mineral oil; liquid petrolatum; white petrolatum; propylene glycol; emulsifying wax; and, water. Alternatively they can be formulated as a suitable lotion or cream, suspended or dissolved in, for example, a mixture of one or more of the following: mineral oil; a polyethylene glycol; liquid paraffin; polysorbate 60; cetyl esters wax; cetearyl alcohol; 2-octyldodecanol; benzyl alcohol and water.

Generally, in humans, oral administration of the compounds of the invention is the preferred route being the most convenient.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regime and route of administration which will be most appropriate for a particular animal.

Thus, according to a further aspect of the invention there is provided a pharmaceutical formulation including a compound of the invention, or a pharmaceutically acceptable salt thereof, or a pharmaceutically acceptable solvate of either entity, in admixture with a pharmaceutically acceptable adjuvant, diluent or carrier.

Preferably, the pharmaceutical formulation is formulated for administration as a single daily dose regime i.e. the formulation has a duration of action of greater than 12 hours and may be, for example, in the form of a controlled release tablet.

According to a further aspect of the invention there is provided a veterinary formulation including a compound of the invention, or a veterinarily acceptable salt thereof, or a pharmaceutically acceptable solvate of either entity, in admixture with a veterinarily acceptable adjuvant, diluent or carrier.

The biological activities and metabolic stabilities of the compounds of the present invention were determined by the following test methods.

Central Nervous System (CNS) Activity

The stimulatory activity of the compounds of the invention on the central nervous system was evaluated in-vitro by recording the excitatory postsynaptic current (EPSC) amplitude in stimulated hippocampal CA1 pyramidal neurones from slices of male Sprague-Dawley rats, as described in more detail hereinafter in the Experimental and Preparations section.

The compounds of the invention typically exhibit a significant increase in EPSC peak amplitude compared with a control sample not including the compound of the invention. Suitably, the compounds of the invention enhance AMPA currents in the CNS.

Metabolic Stability

The metabolic stability of the compounds of the invention was evaluated in-vitro using cryopreserved beagle dog hepatocytes, as described in more detail hereinafter in the Experimental and Preparations section.

The compounds of the invention typically exhibit a significant increase in metabolic stability compared with the control tianeptine. Suitably, the compounds of the invention may exert its therapeutic effect over a prolonged period of time, thereby enabling the patient to benefit from relief of symptoms for a longer period. Furthermore, the patient may only require a once-a-day treatment regime, and as this will usually avoid missed treatments, better compliance is expected.

In addition, treatments with a longer duration of action enable a lower ratio of peak to trough concentrations of active agent in the body for a given frequency of administration and a given level of therapeutic cover, which may result in reduced side effects associated with activity. Suitably, the compounds of the invention may exhibit reduced side effects compared to the control tianeptine, such side effects associated with tianeptine being: gastrointestinal disturbances, such as nausea, constipation and abdominal pain; headache; dizziness; and, changes in dreaming.

EXAMPLES AND PREPARATIONS

Example 1

2-(2-((3-chloro-6-methyl-5,5-dioxido-6,11-dihydrodibenzo[c,f][1.2]thiazepin-1-yl)amino)ethoxy)acetic acid a) 3-chloro-11-((2-hydroxyethyl)amino)-6-methyl-6,11-dihydrodibenzo[c,f][1,2]thiazepine 5,5-dioxide To a solution of 3,11-dichloro-6-methyl-6,11-dihydrodibenzo[c,f][1,2]thiazepine 5,5-dioxide (5 g, 15.2 mmol) in ethanol (50 ml) at 0° C. was added ethanolamine (0.93 g, 15.2 mmol). The reaction mixture was then heated at reflux for 3 hours, it was then cooled to room temperature and a precipitate formed. The precipitate was then filtered and washed with cold ethanol (3×10 ml) to give the desired compound (4.4 g, 82% yield), m.p. 190° C. (dec.), [M/Z M+1=353], $^1$H NMR (300 MHz, CDCl$_3$) δ 1.22 (t, 2H J=7 Hz). 2.01 (s, 2H), 3.25 (s, 3H), 4.09 (t, 2H, J=7 Hz), 5.33 (s, 1H), 7.3-7.6 (m, 7H), 7.95 (s, 1H).

b) 3,11-dichloro-6-methyl-11-((2-(prop-2-yn-1-yloxy)ethyl)amino)-6,11-dihydrodibenzo[c,f][1,2]thiazepine 5,5-dioxide To a stirred solution of 3-chloro-1-((2-hydroxyethyl)amino)-6-methyl-6,11-dihydrodibenzo[c,f][1,2]thiazepine 5,5-dioxide (1 g, 2.83 mmol) in anhydrous tetrahydrofuran (THF) (10 ml) at room temperature under an atmosphere of argon was added sodium hydride (0.125 g, 3.12 mmol, 60% dispersion). The reaction mixture was stirred at room temperature for 1 hour, at which point propargyl bromide (0.37 g, 3.12 mmol) was added drop wise over a 10 minute period. The reaction mixture was then stirred for a further 2 hours. The reaction was then quenched by the addition of water (10 ml) and ethyl acetate (20 ml), the organic layers separated and dried (anhydrous sodium sulphate). The resulting solution was concentrated in vacuo to give the desired compound (1.05 g, 94% yield) as an off white gum, [M/Z M+1=391], $^1$H NMR (300 MHz, CDCl$_3$) δ 1.22 (t, 21-J=7 Hz), 2.09 (s, 2H), 3.28 (s, 3H), 3.4 (s, 1H), 3.62-3.64 (m, 2H), 4.12 (t, 1H, J=7 Hz), 5.02 (s, 1H), 7.3-7.6 (m, 7H), 7.95 (s, 1H). This solid was used without further purification.

c) 2-(2-((3-chloro-6-methyl-5,5-dioxido-6,11-dihydrodibenzo[c,f][1,2]thiazepin-11-yl)amino)ethoxy) acetic acid A flask is charged with a magnetic stirrer, 5 ml of carbon tetrachloride, 5 ml of acetonitrile, 7.5 ml of water, 1 g (2.56 mmol) of 3-chloro-6-methyl-11-((2-(prop-2-yn-1-yloxy) ethyl)amino)-6,11-dihydrodibenzo[c,f][1,2]thiazepine 5,5-dioxide and 2.24 g of sodium metaperiodate. To this biphasic solution, 16 mg of ruthenium trichloride hydrate was added and the reaction mixture stirred vigorously for 2 hours at room temperature. To the reaction mixture, 40 ml of dichloromethane (DCM) was added, and the phases separated. The upper aqueous phase was washed with a further 2×10 ml of DCM. The combined organic phase was dried over anhydrous sodium sulphate and concentrated in vacuo, the resulting residue was then boiled in ether to give a hygroscopic off white amorphous solid (0.81 g, 77% yield), [M/Z M+1=311], $^1$H NMR (300 MHz, D$_6$ DMSO) δ 1.22 (t, 2H J=7 Hz), 2.09 (s, 2H), 3.28 (s, 3H), 3.62 (s, 1H), 4.16 (s, 2H), 5.02 (s, 1H), 7.3-7.6 (m, 7H), 7.95 (s, 1H).

Example 2

2-(4-((3-chloro-6-methyl-5,5-dioxido-6,11-dihydrodibenzo[c,f][1,2]thiazepin-11-yl)amino)butoxy)acetic acid a) t-butyl 2-(4-hydroxybutoxy)acetate

A solution of butane-1,4-diol (10 g, 110.96 mmol) in THF (200 ml) at 0° C. under an atmosphere of argon was treated with sodium hydride (4.4 g, 110.96 mmol, 60% dispersion in oil), the reaction was allowed to warm to room temperature over a period of 1 hour. The crude anion was then cooled to 0° C. and to this solution t-butyl 2-bromoacetate (21.64 g, 110.96 mmol) was added drop wise over 30 minutes whilst the temperature was held below 0° C. The reaction was then quenched with water. The organic phase was separated and washed with brine and dried over anhydrous sodium carbonate. The sample was then concentrated in vacuo to give the desired compound as an oil (16.5 g, 73% yield), $^1$H NMR (300 MHz, CDCl$_3$) δ 1.45 (s, 9H), 1.62-1.72 (m, 2H), 3.51-3.53 (m, 1H), 3.54-3.65 (m, 1H), 3.93 (d, 2H, J=6 Hz), 4.03 (d, 2H, J=4 Hz), 4.1-4.2 (m, 1H). This compound was used without further purification.

b) t-butyl 2-(4-oxobutoxy)acetate t-butyl 2-(4-hydroxybutoxy)acetate (10 g, 48.96 mmol) was dissolved in dichloromethane (350 ml) and stirred at 0° C. in an ice bath. To this solution was added Dess-Martin periodinane (22.84 g, 53.85 mmol) in several portions and the reaction stirred at 0° C. for 1 h. The reaction was quenched at 0° C. by stirring with a solution of Na$_2$S$_2$O$_3$ (68 g in 400 ml water) and NaHCO$_3$ (saturated, aqueous, 400 ml) for 10 min to destroy any unreacted Dess-Martin reagent. The reaction mixture was poured into a separating funnel and extracted with ethyl acetate (3×300 ml). The organic layers were pooled and washed with brine (80 ml), dried over anhydrous magnesium sulphate and concentrated to give 9.7 g (98%) of almost pure product, which was isolated as an oil. $^1$H NMR (300 MHz, CDCl3) δ 1.45 (s, 9H), 1.62-1.72 (m, 1H), 3.51-3.53 (m, 1H), 3.54-3.65 (m, 1H), 3.93 (d, 2H, J=6 Hz), 4.03 (d, 2H, J=4 Hz), 4.1-4.2 (m, 1H) 1H), 9.78 (s, 1H)

c) t-butyl 2-(4-((3-chloro-6-methyl-5,5-dioxido-6,11-dihydrodibenzo[c,f][1,2]thiazepin-11-yl)amino)butoxy)acetate To a stirred suspension of 11-amino-3-chloro-6-methyl-6,11-dihydrodibenzo[c,f][1,2]thiazepine 5,5-dioxide (1.5 g, 4.86 mmol) in dichloroethane (100 ml), triethylamine (2.7 ml, 20 mmol) and t-butyl 2-(4-oxobutoxy)acetate (1.08 g, 5.34 mmol) were added and stirred for half an hour at room temperature under argon. Thereafter sodium triacetoxyborohydride (1.13 g, 5.34 mmol) was added to the reaction mixture with continuous stirring. The reaction mixture was further stirred for 24 hours, then diluted with dichloromethane and washed with 4% aqueous sodium hydroxide solution followed by water. The organic layer was separated and the aqueous layer was extracted with dichloromethane. The combined organic phase was dried over anhydrous sodium sulfate and concentrated to give crude compound (1.4 g) which was brought through to the subsequent step without further purification. [M/Z M+1=439 (−tBu)], $^1$H NMR (300 MHz, CDCl3) δ 1.45 (s, 9H), 1.62-1.72 (m, 2H), 3.28 (s, 3H), 3.51-3.53 (m, 1H), 3.54-3.65 (m, 1H), 3.93 (d, 2H, J=6 Hz), 4.03 (d, 2H, J=4 Hz), 4.1-4.2 (m, 1H), 5.02 (s, 1H), 7.20-7.50 (m, 7H), 7.89 (s, 1H).

d) 2-(4-((3-chloro-6-methyl-5,5-dioxido-6,11-dihydrodibenzo[c,f][1,2]thiazepin-11-yl)amino)butoxy)acetic acid To a solution of t-butyl 2-(4-((3-chloro-6-methyl-5,5-dioxido-6,11-dihydrodibenzo[c,f][1,2]thiazepin-11-yl)amino)butoxy)acetate (1.5 g, 3.03 mmol) in dichloromethane (50 ml) at room temperature was added 5 ml of trifluoroacetic acid. The reaction mixture was stirred at room temperature over 18 hours giving rise to a complex mixture, which was purified by preparative HPLC under basic conditions to give the desired compound as a clear colorless foam (0.26 g, 19% yield). [M/Z M+1=439], $^1$H NMR (300 MHz, CDCl3) δ 1.62-1.72 (m, 2H), 3.28 (s, 3H), 3.51-3.53 (m, 1H), 3.54-3.65 (m, 1H), 3.93 (d, 2H, J=6 Hz), 4.16 (d, 2H, J=4 Hz), 4.1-4.2 (m, 1H) 1H), 5.06 (s, 1H), 7.20-7.50 (m, 7H), 7.89 (s, 1H) 10.5 (broad S, 1H).

Example 3

2-((2-((3-chloro-6-methyl-5,5-dioxido-6,11-dihydrodibenzo[c,f][1,2]thiazepin-11-yl)amino)ethyl)thio)acetic acid a) 3-dichloro-1-((2-mercaptoethyl)amino)-6-methyl-6,11-dihydrodibenzo[c,f][1,2]thiazepine 5,5-dioxide To a solution of 3,11-dichloro-6-methyl-6,11-dihydrodibenzo[c,f][1,2]thiazepine 5,5-dioxide (5 g, 15.2 mmol) and pyridine (2 ml) in ethanol (50 ml) at 0° C. was added thioethanolamine hydrochloride (1.7 g, 15.2 mmol). The reaction mixture was then heated at reflux for 3 hours, it was then cooled to room temperature and a precipitate formed. The precipitate was then filtered and washed with cold ethanol (3×10 ml) to give the desired compound (4.1 g, 73% yield) as a amorphous solid, m.p. 230° C. (dec.), [M/Z M+1=369], $^1$H NMR (300 MHz, CDCl$_3$) δ 1.29 (t, 2H J=7 Hz), 2.01 (t, 2H, J=7 Hz), 3.24 (s, 3H), 5.76 (s, 1H), 7.28-7.6 (m, 7H), 7.96 (s, 1H).

b) 2-((2-((3-chloro-6-methyl-5,5-dioxido-6,11-dihydrodibenzo[c,f][1,2]thiazepin-11-yl)amino)ethyl)thio)acetic acid To a stirred solution of 3-chloro-11-((2-mercaptoethyl)amino)-6-methyl-6,11-dihydrodibenzo[c,f][1,2]thiazepine 5,5-dioxide (2 g, 5.42 mmol) in acetonitrile (20 ml) at room temperature, was added potassium carbonate (1.5 g, 10.84 mmol) and iodoacetic acid (1.01 g, 5.42 mmol). The reaction was stirred at room temperature for a further 18 hours, then diluted with water (50 ml) and ethyl acetate (40 ml). The organic layer was separated, washed with brine and dried (anhydrous MgSO$_4$). The organic layer was then concentrated in vacuo to give the desired compound (1.3 g, 56% yield) as a cream coloured foam. [M/Z M+1=427], $^1$H NMR (300 MHz, CDCl$_3$) δ 1.29 (t, 2H J=7 Hz), 2.01 (t, 2H, J=7 Hz), 3.24 (s, 3H), 3.75 (s, 2H), 5.91 (s, 1H), 7.28-7.6 (m, 7H), 7.96 (s, 1H).

Example 4

2-((2-((3-chloro-6-methyl-5,5-dioxido-6,11-dihydrodibenzo[c,f][1,2]thiazepin-11-yl)amino)ethyl)sulfonyl)acetic acid To a stirred solution of 2-((2-((3-chloro-6-methyl-5,5-dioxido-6,11-dihydrodibenzo[c,f][1,2]thiazepin-11-yl)amino)ethyl)thio)acetic acid (0.5 g, 1.17 mmol) in methanol (20 ml) at room temperature, was added Oxone (0.16 g, 1.17 mmol). The reaction was stirred at room temperature for a further 18 hours, and then diluted with water (50 ml) and ethyl acetate (40 ml). The organic layer was separated, washed (1×20 ml water, 1×20 ml brine), dried (anhydrous $Na_2SO_4$) and concentrated in vacuo to give the desired compound as a tan coloured gum (0.54 g, 100% yield). [M/Z M+1=459], $^1$H NMR (300 MHz, $CDCl_3$) δ 1.29 (t, 2H J=7 Hz), 2.37 (t, 2H, J=7 Hz), 3.24 (s, 3H), 4.28 (s, 2H), 5.91 (s, 1H), 7.28-7.6 (m, 7H), 7.96 (s, 1H).

Example 5

5-((3-chloro-6-methyl-5,5-dioxido-6,11-dihydrodibenzo[c,f][1.2]thiazepin-11-yl)amino)pentanamide a) 5-((t-butoxycarbonyl)amino)pentanoic acid

To a solution containing 5-aminovaleric acid (5.85 g, 0.05 mol) in 100 ml of 2 percent aqueous sodium hydroxide and 100 ml of dioxane was dropwise added a solution containing di-t-butyldicarbonate (10.9 g, 0.05 mol) in 40 ml of dioxane. The reaction mixture was stirred for 18 hours and then acidified to pH3 using 1N hydrochloric acid. The acidified mixture was extracted three times with dichloromethane. The organic layers were combined, washed with water, and dried over anhydrous sodium sulfate to yield 10.1 g (93.5% yield) of the desired compound as a white crystalline solid, m.p. 47-49° C.

b) t-butyl (5-amino-5-oxopentyl)carbamate

Isobutyl chloroformate (1.55 ml, 12 mmol) in tetrahydrofuran (5 ml) was added dropwise over approximately 5 minutes to a vigorously stirred solution of 5-((t-butoxycarbonyl)amino)pentanoic acid (2.61 g., 12 mmol) and N-methylmorpholine (1.32 ml., 12 mmol) in tetrahydrofuran (15 ml) at −15° C., while maintaining the reaction temperature between −25° C. and −15° C. The reaction mixture was stirred for 12 minutes, and then 10 ml of a solution of ammonia in methanol (saturated at 0° C.) was added dropwise over 30 minutes at approximately −15° C. The reaction mixture was stirred an additional 30 minutes in the cold, and then allowed to warm to room temperature and left to stir overnight. The thick white suspension was diluted with water, concentrated in vacuo to remove organic solvents and then extracted with ethyl acetate (150 ml). The ethyl acetate solution was washed with water, 10% potassium bisulfate, water and brine, dried (anhydrous sodium sulphate), and evaporated to give 1.54 g (59% yield) of white solid product; m.p. 136-139° C., [M/Z M+1=217 & 161 (−tBu)].

c) 5-aminopentanamide hydrochloride

To a solution of 1-butyl (5-amino-5-oxypentyl)carbamate (1.5 g, 6.94 mmol) in ether (20 ml) was added 1M hydrochloric acid in dioxane (10 ml) and the reaction mixture stirred for 1 hour. The precipitate was filtered and washed with cold ether, to give the desired compound as a white foam (1 g, 98% yield). $^1$H NMR (300 MHz, $D_6$ DMSO) δ 1.50 (s, 2H), 2.04 (s, 2H), 2.46 (s, 2H), 2.69 (app d, 2H), 7.34 (s, 2H), 8.04 (s, 3H).

d) 5-((3-chloro-6-methyl-5,5-dioxido-6,11-dihydrodibenzo[c,f][1,2]thiazepin-11-yl)amino)pentanamide To a solution of 3,11-dichloro-6-methyl-6,11-dihydrodibenzo[c,f][1,2]thiazepine 5,5-dioxide (1 g, 3.05 mmol) in acetonitrile (50 ml) at 0° C. was added triethylamine (2 ml), followed by addition of 5-aminopentamide hydrochloride (0.465 g, 3.05 mmol) and the mixture stirred for 1 hour. The reaction mixture was then concentrated in vacuo to give the crude product as oil. The product was then isolated by flash chromatography (eluent methanol:dichloromethane (1:10)) to give 0.85 g (68% yield) of the desired compound as an tan foam. [M/Z M+1=408], $^1$H NMR (300 MHz, $CDCl_3$) δ 1.23-1.26 (m, 4H), 2.05 (s, 2H), 2.1 (s, 1H), 2.15 (s, 1H), 3.19 (s, 3H) 5.68 (s, 1H), 7.20-7.50 (m, 7H), 7.93 (s, 1H).

Example 6

Ethyl 5-((3-chloro-6-methyl-5,5-dioxido-6,11-dihydrodibenzo[c,f][1,2]thiazepin-11-yl)amino)-3,3-dimethylpentanoate a) 5-ethoxy-3,3-dimethyl-5-oxopentanoic acid

A suspension of 3,3-dimethylglutaric anhydride (9.0 g, 63.4 mmol) and dimethylaminopyridine (0.77 g, 6.3 mmol) in triethylamine (8.8 ml, 63.4 mmol) and ethanol (75 ml) was heated at reflux overnight. The ethanol was removed in vacuo, and the residue was then dissolved in ethyl acetate (150 ml), washed successively with citric acid (1 M, 3×100 ml), water and dried over $MgSO_4$, and concentrated in vacuo to afford the desired compound (11.06 g, 100%) as a colourless oil which was used in the next step without further purification. [M/Z M+1=188].

b) ethyl 5-hydroxy-3,3-dimethylpentanoate

To a solution of 5-ethoxy-3,3-dimethyl-5-oxopentanoic acid (10 g, 53.3 mmol) in THF (250 ml) was added 1M borane THF (53.3 ml) over a period of 1 hour. The reaction mixture was stirred at room temperature for 6 hours, then methanol (100 ml) was added to the reaction mixture and concentrated in vacuo. This was repeated a further 2 times to give the desired compound (9 g, 97%) as a colourless oil which was used in the next step without further purification. [M/Z M+1=174].

c) ethyl 3,3-dimethyl-5-oxopentanoate

Ethyl 5-hydroxy-3,3-dimethylpentanoate (8.5 g, 48.8 mmol) was dissolved in dichloromethane (350 ml) and stirred at 0° C. in an ice bath. To this solution was added Dess-Martin periodinane (22.76 g, 53.7 mmol) in several portions and the reaction stirred at 0° C. for 1 hour. The reaction was quenched at 0° C. by stirring with a solution of $Na_2S_2O_3$ (68 g in 400 ml water) and $NaHCO_3$ (saturated, aqueous, 400 ml) for 10 min to destroy any unreacted Dess-Martin reagent. The reaction mixture was poured into a separating funnel and extracted with ethyl acetate (3×300 ml). The organic layers were pooled and washed with brine (80 ml), dried over anhydrous magnesium sulphate and concentrated in vacuo to give 8.05 g (95% yield) of almost pure product, which was isolated as an oil. [M/Z M+1=186]. $^1$H NMR (300 MHz, $CDCl_3$) (1.15 (s, 6H), 2.40 (s, 2H), 2.50 (m, 2H), 3.12 (d, 3H, J=7 Hz), 4.10 (m, 2H) 9.85 (s 1H).

d) ethyl 5-((3-chloro-6-methyl-5,5-dioxido-6,11-dihydrodibenzo[c,f][1,2]thiazepin-11-yl)amino)-3,3-dimethylpentanoate To a stirred suspension of 11-amino-3-chloro-6-methyl-6,11-dihydrodibenzo[c,f][1,2]thiazepine 5,5-dioxide (1.5 g, 4.86 mmol) in dichloroethane (100 ml), triethylamine (2.7 ml, 20 mmol) and ethyl 3,3-dimethyl-5-oxopentanoate (0.92 g, 5.34 mmol) were added and stirred for half an hour at room temperature under argon. Thereafter sodium triacetoxyborohydride (1.13 g, 5.34 mmol) was added to the reaction mixture with continuous stirring and then the reaction mixture was further stirred for 24 hours. The reaction mixture was then diluted with dichloromethane and washed with 4% aqueous sodium hydroxide solution followed by water. The organic layer was separated and the aqueous layer was extracted with dichloromethane. The combined organic phase was dried over anhydrous sodium sulfate and concentrated to give crude compound (2.1 g) which was brought through to the subsequent step. [M/Z M+1=466] $^1$H NMR (300 MHz, CDCl3) δ 1.22 (s, 6H), 2.39 (s, 2H), 2.61 (broad m, 2H), 3.12 (d, 3H, J=7 Hz), 3.24 (s, 3H), 4.10 (m, 2H), 5.47 (s, 1H), 7.3-7.6 (m, 7H), 7.91 (s, 1H).

Metabolic Stability

The test compound (1 µM) was incubated with cryopreserved beagle dog hepatocytes at 3 million cells per ml, in 300 µL of Leibovitz's medium for a total period of 90 min. During this period, 25 µL aliquots were taken at 1, 10, 30, 50, 70 & 90 minutes and quenched in acetonitrile. Quenched samples were centrifuged to pellet the precipitated protein, and supernatant removed for LC-MS-MS (high performance liquid chromatography coupled to a tandem mass spectrometer) analysis to quantify the amount of the parent test compound remaining. The first order elimination rate constant (k) was determined from a plot of natural log of parent test compound remaining versus time, and used to calculate a metabolic stability half-life ($T_{1/2}$), where $T_{1/2}$=Ln2/k where k=elimination rate constant. The results are shown in the table below:

| | $Cl_{int}$ (µL/min/$10^6$ cells) | $t_{1/2}$ (mins) | PPB, % bound | PPB, $F_u$ |
|---|---|---|---|---|
| Tianeptine | 4.5 | 155 | 92 | 0.08 |
| Example 2 | 0.3 | 2062 | 82 | 0.18 |

$Cl_{int}$ represents intrinsic clearance calculated as the rate of disappearance of the test compound in units of µL/min/million cells
PPB, % bound represents percentage of compound bound to proteins
PPB, $F_u$ represents fraction of compound not bound to proteins The metabolic stability half life of a compound of Example 2 (2062 minutes) is more than 10 times the metabolic stability half life of tianeptine (155 minutes). Moreover, the fraction of the amount of a compound of Example 2 which is not protein bound (PPB, $F_u$ of 0.18) is more than doubled compared with tianeptine (PPB, $F_u$ of 0.08), thereby indicating that a compound of the invention is potentially more suited for coadministration with a further pharmaceutical active agent than tianeptine.

Electrophysiological (CNS) Activity

Slice Preparation

Male Sprague-Dawley rats, 15 to 20 days old at the time of surgery, were used in this study. On the day of the experiment, animals were terminally anaesthetized using isofluorane, cervically dislocated, and decapitated. The brain was removed and 400 µm thick parasagittal brain slices prepared using a Leica VT1000S. Slices were maintained in an artificial cerebrospinal fluid (ACSF) of the following composition (in mM, aqueous solution): 127 NaCl; 1.9 KCl; 1.2 $KH_2PO_4$; 2.4 $CaCl_2$; 1.3 $MgCl_2$; 26 $NaHCO_3$; and, 10 D-glucose, bubbled with a mixture of 95% $O_2$/5% $CO_2$, at room temperature for 1 hour after slicing before commencing electrophysiological recordings.

Whole Cell Recordings

Whole cell recordings of AMPA-kainate EPSCs from hippocampal CA1 commissural associational (c/a) synapses may be obtained using methods known to those skilled in the art, for example, by the method of Kole (Eur. J. Neurosci 16, 807-816 (2002). In particular, one hour after slice preparation, individual slices were transferred to a custom-built chamber continuously perfused with ACSF at a rate of 4-10 ml·min$^{-1}$ of the following composition (in mM, aqueous solution): 127 NaCl; 1.9 KCl; 1.2 $KH_2PO_4$; 2.4 $CaCl_2$; 1.3 $MgCl_2$; 26 $NaHCO_3$; and, 10 D-glucose, equilibrated with a mixture of 95% $O_2$/5% $CO_2$. Whole-cell recordings were performed at room temperature from hippocampal CA1 pyramidal neurones using the 'visualised' version of the patch-clamp technique using a Multiclamp 700B amplifier. Patch pipette electrodes were pulled from thin-walled borosilicate glass and had resistances of between 3 and 8 MΩ when filled with the intracellular aqueous solution of the following composition (in mM): 140 K-gluconate; 10 KCl; 1 EGTA-Na; 10 HEPES; 2 $Na_2$ATP. Osmolarity and pH were adjusted with sucrose and KOH, respectively, to 310 mOsm and 7.4, respectively). Synaptic responses were evoked with a bipolar concentric stimulating electrode placed within the Schaffer collateral pathway in order to stimulate postsynaptic currents in the recorded neurone and positioned 200-500 µm subjacent to the recording pipette. Stimuli were 1-10 V and 0.2 s duration. A stimulation frequency of 0.1 Hz was used. The values of synaptic currents represent the average of 6 experiments. Recordings were performed at room temperature. Control EPSC levels (i.e. in the absence of a test compound) were recorded for at least 10 minutes prior to test compound application. The test compounds 10 µM were bath applied. A representative electrophysiological recording of the compound of Example 2 is shown in FIG. 1 which demonstrates the compound facilitates excitatory transmission in CA region of hippocampus. Changes in EPSC parameters were calculated as a percentage of the control and are expressed as mean±S.E.M (n=6).

Bath application of 10 µM of the compound of Example 2 increased control EPSC amplitude by 224.67±34.27% with mean EPSC amplitude rising from −44.06±6.06 pA to 94.88±17.42 pA upon application.

The invention claimed is:

1. A compound of formula I:

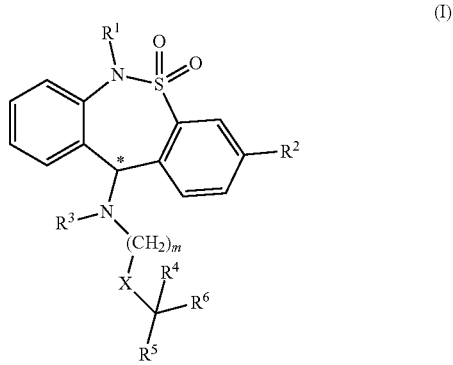

(I)

or a pharmaceutically or veterinarily acceptable salt thereof,
wherein:
$R^1$ and $R^3$ each independently represent, at each occurrence when used herein, H or $C_1$ to $C_6$ alkyl;
$R^2$ represents halo;
$R^4$ and $R^5$ each independently represent, at each occurrence when used herein, H, $C_1$ to $C_6$ alkyl, $C_2$ to $C_6$ alkenyl or $R^4$ and $R^5$ together form a 3, 4 or 5-membered alicyclic ring, wherein each of said alkyl and alkenyl groups are each independently optionally interrupted by one or more of —O—, —S— or —N($R^7$)— and/or substituted and/or terminated by one or more substituents selected from halo, —CN, —$NO_2$, —C(O)N($R^7$)$R^8$, —C(O)$R^7$, —C(O)O$R^7$, —N($R^7$)$R^8$, —O$R^7$;
$R^6$ represents —C(O)O$R^9$, —S(O)$_2$O$R^9$ or —C(O)N($R^7$)$R^8$;
X represents O, N($R^7$), S, S(=O), S(O)$_2$ or C($R^{10}$)($R^{11}$);
$R^7$ and $R^8$ each independently represent, at each occurrence when used herein, H or $C_1$ to $C_6$ alkyl;
$R^9$ represents H, $C_1$ to $C_6$ alkyl or $C_2$ to $C_6$ alkenyl, wherein each of said alkyl and alkenyl groups are each independently optionally interrupted by one or more of —O—, —S— or —N($R^7$)— and/or substituted and/or terminated by one or more substituents selected from halo, —CN, —$NO_2$, —C(O)N($R^7$)$R^8$, —C(O)$R^7$, —C(O)O$R^7$, —N($R^7$)$R^8$, —O$R^7$;
$R^{10}$ and $R^{11}$ each independently represent, at each occurrence when used herein, H, $C_1$ to $C_6$ alkyl, $C_2$ to $C_6$ alkenyl or $R^{10}$ and $R^{11}$ together form a 3, 4 or 5-membered alicyclic ring, wherein each of said alkyl and alkenyl groups are each independently optionally interrupted by one or more of —O—, —S— or —N($R^7$)— and/or substituted and/or terminated by one or more substituents selected from halo, —CN, —$NO_2$, —C(O)N($R^7$)$R^8$, —C(O)$R^7$, —C(O)O$R^7$, —N($R^7$)$R^8$, —O$R^7$; and,
m is an integer from 1 to 10 inclusive;
with the proviso that when X represents C($R^{10}$)($R^{11}$) then at least one of $R^4$, $R^5$, $R^{10}$, $R^{11}$ is not H.

2. A compound as claimed in claim 1, wherein $R^1$ represents $C_1$ to $C_6$ alkyl.

3. A compound as claimed in claim 1, wherein $R^2$ represents chloro.

4. A compound as claimed in claim 1, wherein $R^3$ represents H or $C_1$ to $C_4$ alkyl.

5. A compound as claimed in claim 1, wherein $R^4$ and $R^5$ each independently represent H, $C_1$ to $C_6$ alkyl, $C_2$ to $C_6$ alkenyl or $R^4$ and $R^5$ together form a 3, 4 or 5-membered alicyclic ring.

6. A compound as claimed in claim 5, wherein $R^4$ and $R^5$ each independently represent H or $C_1$ to $C_6$ alkyl.

7. A compound as claimed in claim 1, wherein $R^4$ and $R^5$ are both identical.

8. A compound as claimed in claim 1, wherein $R^6$ represents —C(O)O$R^9$ or —C(O)N($R^7$)$R^8$.

9. A compound as claimed in claim 1, wherein $R^9$ represents H or $C_1$ to $C_6$ alkyl.

10. A compound as claimed in claim 1, wherein X represents C($R^{10}$)($R^{11}$) and $R^{19}$ and $R^{11}$ each independently represent H, $C_1$ to $C_6$ alkyl, $C_2$ to $C_6$ alkenyl or $R^{10}$ and $R^{11}$ together form a 3, 4 or 5-membered alicyclic ring.

11. A compound as claimed in claim 10, wherein $R^{10}$ and $R^{11}$ each independently represent H or $C_1$ to $C_6$ alkyl.

12. A compound as claimed in claim 1, wherein $R^{10}$ and $R^{11}$ are both identical.

13. A compound as claimed in claim 1, wherein X represents O, S, S(=O), S(O)$_2$ or N($R^7$).

14. A compound as claimed in claim 1, wherein m is 1 to 4 inclusive.

15. A compound as claimed in claim 1, wherein:
$R^1$ represents methyl;
$R^2$ represents chloro;
$R^3$ represents H;
$R^4$ and $R^5$ both represent H;
$R^6$ represents —C(O)O$R^9$;
$R^9$ represents H;
X represents O; and, m is 4.

16. A compound as claimed in claim 1, wherein the compound of formula (I) comprises substantially the (R) or (S) enantiomer, in respect of the aliphatic carbon marked with an asterisk (*) in formula (I).

17. A compound of formula (II), (III) or (VII):

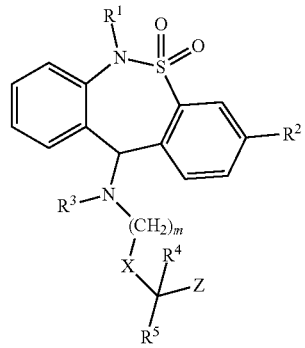

(II)

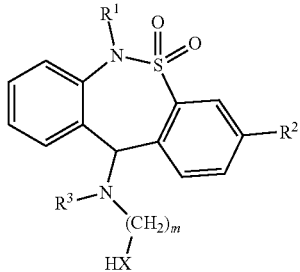

(III)

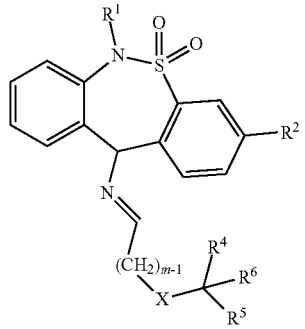

(VII)

wherein:
$R^1$ and $R^3$ each independently represent, at each occurrence when used herein, H or $C_1$ to $C_6$ alkyl;
$R^2$ represents halo;
$R^4$ and $R^5$ each independently represent, at each occurrence when used herein, H, $C_1$ to $C_6$ alkyl, $C_2$ to $C_6$ alkenyl or $R^4$ and $R^5$ together form a 3, 4 or 5-membered alicyclic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^6$ represents —C(O)OR$^9$, —S(O)$_2$OR$^9$ or —C(O)N(R$^7$)R$^8$;

R$^7$ and R$^8$ each independently represent, at each occurrence when used herein, H or C$_1$ to C$_6$ alkyl;

R$^9$ represents H, C$_1$ to C$_6$ alkyl or C$_2$ to C$_6$ alkenyl, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^{10}$ and R$^{11}$ each independently represent, at each occurrence when used herein, H, C$_1$ to C$_6$ alkyl, C$_2$ to C$_6$ alkenyl or R$^{10}$ and R$^{11}$ together form a 3, 4 or 5-membered alicyclic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$; and, m is an integer from 1 to 10 inclusive;

with the proviso that when X represents C(R$^{10}$)(R$^{11}$) then at least one of R$^4$, R$^5$, R$^{10}$, R$^{11}$ is not H;

X in a compound of formulae (II) and (VII) is defined as O, N(R$^7$), S, S(═O), S(O)$_2$ or C(R$^{10}$)(R$^{11}$); and X in a compound of formula (III) represents N(R$^7$) or S, and Z in a compound of formula (II) represents —C≡CH group or —SH.

18. A pharmaceutical composition comprising a compound of formula (I) as claimed in claim 1, or a pharmaceutically acceptable salt thereof, together with a pharmaceutically acceptable adjuvant, diluent or carrier.

19. A pharmaceutical composition as claimed in claim 18, wherein the composition has a duration of action of more than 12 hours.

20. A pharmaceutical composition as claimed in claim 18, wherein the composition is suitable for oral administration.

21. A pharmaceutical composition as claimed in claim 18, wherein the composition is suitable for inhaled or topical administration.

22. A process for the preparation of a compound of claim 1, or a pharmaceutically acceptable salt thereof, comprising oxidizing the —C≡CH group or the thiol group in a compound the formula (II):

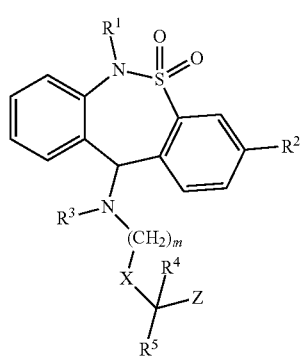

(II)

wherein R$^1$ and R$^3$ each independently represent, at each occurrence when used herein, H or C$_1$ to C$_6$ alkyl;

R$^2$ represents halo;

R$^4$ and R$^5$ each independently represent, at each occurrence when used herein, H, C$_1$ to C$_6$ alkyl, C$_2$ to C$_6$ alkenyl or R$^4$ and R$^5$ together form a 3, 4 or 5-membered alicyclic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^6$ represents —C(O)OR$^9$, —S(O)$_2$OR$^9$ or —C(O)N(R$^7$)R$^8$;

X represents O, N(R$^7$), S, S(═O), S(O)$_2$ or C(R$^{10}$)(R$^{11}$);

R$^7$ and R$^8$ each independently represent, at each occurrence when used herein, H or C$_1$ to C$_6$ alkyl;

R$^9$ represents H, C$_1$ to C$_6$ alkyl or C$_2$ to C$_6$ alkenyl, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^{10}$ and R$^{11}$ each independently represent, at each occurrence when used herein, H, C$_1$ to C$_6$ alkyl, C$_2$ to C$_6$ alkenyl or R$^{10}$ and R$^{11}$ together form a 3, 4 or 5-membered alicyclic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

and, m is an integer from 1 to 10 inclusive;

with the proviso that when X represents C(R$^{10}$)(R$^{11}$) then at least one of R$^4$, R$^5$, R$^{10}$, R$^{11}$ is not H, and Z represents —C≡CH or —SH.

23. A process for the preparation of a compound of claim 1, or a pharmaceutically acceptable salt thereof, comprising reducing a compound of formula (VII):

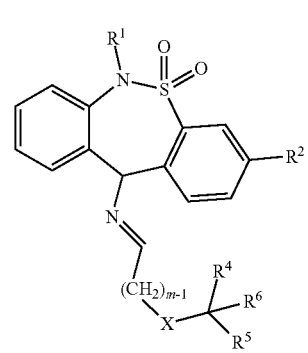

(VII)

wherein R$^1$ and R$^3$ each independently represent, at each occurrence when used herein, H or C$_1$ to C$_6$ alkyl;

R$^2$ represents halo;

R$^4$ and R$^5$ each independently represent, at each occurrence when used herein, H, C$_1$ to C$_6$ alkyl, C$_2$ to C$_6$ alkenyl or R$^4$ and R$^5$ together form a 3, 4 or 5-membered alicyclic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^6$ represents —C(O)OR$^9$, —S(O)$_2$OR$^9$ or —C(O)N(R$^7$)R$^8$;

X represents O, N(R$^7$), S, S(=O), S(O)$_2$ or C(R$^{10}$)(R$^{11}$);

R$^7$ and R$^8$ each independently represent, at each occurrence when used herein, H or C$_1$ to C$_6$ alkyl;

R$^9$ represents H, C$_1$ to C$_6$ alkyl or C$_2$ to C$_6$ alkenyl, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$;

R$^{10}$ and R$^{11}$ each independently represent, at each occurrence when used herein, H, C$_1$ to C$_6$ alkyl, C$_2$ to C$_6$ alkenyl or R$^{10}$ and R$^{11}$ together form a 3, 4 or 5-membered alicylic ring, wherein each of said alkyl and alkenyl groups are each independently optionally interrupted by one or more of —O—, —S— or —N(R$^7$)— and/or substituted and/or terminated by one or more substituents selected from halo, —CN, —NO$_2$, —C(O)N(R$^7$)R$^8$, —C(O)R$^7$, —C(O)OR$^7$, —N(R$^7$)R$^8$, —OR$^7$; and, m is an integer from 1 to 10 inclusive;

with the proviso that when X represents C(R$^{10}$)(R$^{11}$) then at least one of R$^4$, R$^5$, R$^{10}$, R$^{11}$ is not H.

24. The compound as claimed in claim 2, wherein R$^1$ represents methyl.

25. The compound as claimed in claim 4, wherein R$^3$ represents H.

26. The compound as claimed in claim 7, wherein R$^4$ and R$^5$ are both H.

27. The compound as claimed in claim 8, wherein R$^6$ represents —C(O)OR$^9$.

28. The compound as claimed in claim 9, wherein R$^9$ represents H.

29. The compound as claimed in claim 11, wherein R$^{10}$ and R$^{11}$ each independently represent C$_1$ to C$_6$ alkyl.

30. The compound as claimed in claim 13, wherein X represents O.

* * * * *

UNITED STATES PATENT AND TRADEMARK OFFICE
CERTIFICATE OF CORRECTION

PATENT NO. : 9,487,492 B2
APPLICATION NO. : 14/112499
DATED : November 8, 2016
INVENTOR(S) : David Cavalla It is certified that error appears in the above-identified patent and that said Letters Patent is hereby corrected as shown below:

In the Claims

In Claim 10, Column 27, Line 61, after the word "and", please change "$R^{19}$" to --$R^{10}$--.

Signed and Sealed this
Third Day of January, 2017

Michelle K. Lee
*Director of the United States Patent and Trademark Office*